United States Patent
Wu et al.

(10) Patent No.: US 9,506,096 B2
(45) Date of Patent: Nov. 29, 2016

(54) SUGAR PREPARATION PROCESS BY ENZYMATICALLY HYDROLYZING SWEET POTATO DREG

(71) Applicant: SHANDONG HONGHE SUNKEEN BIOTECHNOLOGY CO. LTD., Zoucheng (CN)

(72) Inventors: Yunshan Wu, Zoucheng (CN); Gonghong Yan, Zoucheng (CN); Yong Yi, Zoucheng (CN); Zheng'en Kou, Zoucheng (CN); Zhen Wu, Zoucheng (CN)

(73) Assignee: SHANDONG HONGHE SUNKEEN BIOTECHNOLOGY CO. LTD., Zoucheng (CN)

( * ) Notice: Subject to any disclaimer, the term of this patent is extended or adjusted under 35 U.S.C. 154(b) by 67 days.

(21) Appl. No.: 14/385,817

(22) PCT Filed: Apr. 1, 2013

(86) PCT No.: PCT/CN2013/073545
§ 371 (c)(1),
(2) Date: Sep. 17, 2014

(87) PCT Pub. No.: WO2013/143503
PCT Pub. Date: Oct. 3, 2013

(65) Prior Publication Data
US 2015/0044730 A1 Feb. 12, 2015

(30) Foreign Application Priority Data
Mar. 30, 2012 (CN) .......................... 2012 1 0090800

(51) Int. Cl.
*C12P 7/10* (2006.01)
*C12P 19/02* (2006.01)
*C13K 1/06* (2006.01)
*C12P 19/14* (2006.01)
*A23L 1/09* (2006.01)

(52) U.S. Cl.
CPC ............... *C12P 19/02* (2013.01); *A23L 1/095* (2013.01); *C12P 19/14* (2013.01); *C13K 1/06* (2013.01)

(58) Field of Classification Search
None
See application file for complete search history.

(56) References Cited

U.S. PATENT DOCUMENTS

| 2006/0275882 A1 | 12/2006 | Martinez-Gutierrez et al. |
| 2009/0093027 A1 | 4/2009 | Balan et al. |
| 2009/0203101 A1 | 8/2009 | Breneman et al. |

FOREIGN PATENT DOCUMENTS

| CN | 1970781 A | 5/2007 | |
| CN | 101173256 A | 5/2008 | |
| CN | 101240310 A * | 8/2008 | ............... C12N 9/14 |
| CN | 101434977 A | 5/2009 | |
| CN | 101676397 A | 3/2010 | |
| CN | 101689638 A | 3/2010 | |
| CN | 102286446 A | 12/2011 | |
| CN | 102559811 | 7/2012 | |
| CN | 102618602 A | 8/2012 | |
| WO | WO 2004/087889 | 10/2004 | |
| WO | WO 2007/071818 | 6/2007 | |
| WO | WO 2009/052101 | 4/2009 | |
| WO | WO 2012093041 A1 * | 7/2012 | .............. C12P 5/023 |

OTHER PUBLICATIONS

Chimata et al., "Fermentative Production and Thermostability Characterization of a Amylase from Aspergillus Species and Its Application Potential Evaluation in Desizing of Cotton Cloth", Biotechnology Research International 2011, vol. 2011, Article ID # 323891, pp. 1-8.*
Berlin et al., "Optimization of Enzyme Complexes for Lignocellulose Hydrolysis," *Biotechnology and Bioengineering*, 97(20): 287-296 (2007).
Du, Lianqi, "Investigation on the Optimum Hydrolysis Conditions of Sweet Potato Pulp Sugar," *Modern Business Trade Industry*, 11(1): 44-45 (1999).
Xin-fang, Gong et al., "Investigation on the Fed-batch Hydrolysis of Cassava Pulp by Multi-Enzymes and Ethanol Fermentation by *Saccharomyces cerevisiae*," *Food and Fermentation Industries*, 37(4) 112-116 (2011).
PCT International Search Report issued in International Application No. PCT/CN2013/073545, mailed Jul. 13, 2013.
Yue et al., "Optimization of Fermentation Conditions for Raw Starch Residue of Potatoes," *Chemical Industry and Engineering*, 28(2): 49-54 (2011). (Chinese only).
Extended European Search Report issued in European patent application No. 13770343.5, dated Oct. 16, 2015.
Shariffa et al., "Enzymatic hydrolysis of granular native and mildly heat-treated tapioca and sweet potato starches at sub-gelatinization temperature," *Food Hydrocolloids*, 23(2):434-440, 2009.

* cited by examiner

*Primary Examiner* — Renee Claytor
*Assistant Examiner* — Michelle F Paguio Frising
(74) *Attorney, Agent, or Firm* — Parker Highlander PLLC

(57) ABSTRACT

The present invention relates to the field of biology, in particular to a sugar preparation method by using biomass sweet potato dregs for microbial fermentation as a sugar source. The liquid sugar product prepared with the method of the present invention essentially comprises the ingredient of glucose. The method of the present invention is of simple process, high specificity, good product quality and high yield, and solves the serious environmental pollution problem of the sweet potato dregs, thus having a good industrial application prospect.

11 Claims, No Drawings

SUGAR PREPARATION PROCESS BY ENZYMATICALLY HYDROLYZING SWEET POTATO DREG

This application is a national phase application under 35 U.S.C. §371 of International Application No. PCT/CN2013/073545, filed Apr. 1, 2013, which claims the priority of China Patent Application No. 201210090800.8, filed with the Patent Office of China on Mar. 30, 2012, titled "SUGAR PREPARATION PROCESS BY ENZYMATICALLY HYDROLYZING SWEET POTATO DREG". The entire contents of the above-referenced disclosures are specifically incorporated herein by reference.

FIELD OF THE INVENTION

The present invention relates to the field of biology, in particular to a sugar preparation method by using biomass of sweet potato residue as sugar source for microbial fermentation.

BACKGROUND OF THE INVENTION

Sweet potato is one of the most important food crops in our country. According to statistics, sweet potato cultivation and processing in our country rank first in the world, and the total production reaches 85.2 million tons, wherein 55% of it (about 46.86 million tons) turns into industrial raw materials. Sweet potato residue is the plenty of residue produced in the process of processing fresh sweet potato into starch, and is disposed as waste. Therefore, huge renewable resources of biomass have yet been developed and utilized.

Fresh sweet potato generally contains 30% dry matter and 70% moisture. Plenty of waste water containing cell sap is produced in the processing of sweet potato, which is the sweet potato starch waste water. It contains various nutritious organic substances, such as soluble carbohydrates, proteins, vitamins and trace elements. The residue of sweet potato starch processing is analyzed, and the main chemical ingredients are water, starch, crude protein, fiber, fat, etc.

The waste residue of sweet potato produced by finely processing sweet potato to produce starch, vermicelli, instant noodle, starch noodle, etc. accounts for about 10% of the raw materials. The fresh sweet potato residue immediately from the production line generally contains about 90% of the cell sap. Plenty of wet sweet potato residue piles up, and is not effectively developed and utilized. Furthermore, due to the high water holding capacity and swelling capacity of the sweet potato fibers, fresh residue of sweet potato having sugar, nitrogen and various nutritious ingredients contains 90% water, and the chemical oxygen demand (COD) of the waste water thereof >15000 mg/L. Therefore, the residue is susceptible to rancidification caused by fermentation of miscellaneous bacteria, severely pollutes the environment, and leads to huge waste of renewable resources of biomass.

In recent years, the hotspot for developing sweet potato residue includes using acid method, enzymatic method and screening method to remove the majority of starch, protein and fat in the sweet potato residue, to extract dietary fiber and pectin, and prepare them into products. However, the market demand for such products was weak, and they have not been produced in large industrial scales.

The sweet potato residue contains, based on dry weight, more than 50% starch and 22~26% fiber. The fiber is mainly composed of cellulose, hemicellulose, lignin and pectin, etc., and it is the carbohydrate of thousands of glucose groups in dense structure, which is difficult to be degraded by commercially available cellulase secreted by *Trichoderma koningii*. The starch produced by pulverizing with a rasping machine and subjecting to a sifting machine is separated. The remaining starch in the sweet potato residue is liquified by α-amylase and saccharified by glucoamylase, and the degradation thereof is not complete. Therefore, it is an important task for performing comprehensive utilization of the waste resources of biomass sweet potato residue, to find a method capable of efficiently transforming sweet potato residue into glucose and developing a new source of sugar, and to industrialize the method. Such non-food source of sugar has significant environmental benefit, social benefit, and economic benefit.

SUMMARY OF THE INVENTION

The objective of the present invention is to provide a method for preparing sugar comprising enzymatic multiple-component biochemical degradation reaction, by using combined multi-enzymatic hydrolysis to destroy the cell wall having several polysaccharide components in the sweet potato residue and to release monomers. This method improves the conversion rate of glucose, and ensures the purity of the sugar products.

The present invention provides a method for preparing sugar by using sweet potato residue, which comprises the following steps.

Step 1: taking sweet potato residue, pulverizing or grinding the wet residue, adding the waste water of sweet potato starch to formulate a slurry; adjusting the slurry to pH 4.0~6.0, adding cellulase and adding β-glucanase to hydrolyze for 2~10 h at 20~70° C.

Step 2: adding xylanase and pectinase to hydrolyze for 2~10 h at 25~60° C. and pH 3.5~6.0; adding acid protease to hydrolyze for 1~8 h at a temperature of 30~50° C. and pH 2.5~6.0; heating at 110~120° C. for 30 min to inactivate the enzymes; adjusting to pH 5.5~8.0, adding thermostable α-amylase or mesophilic α-amylase to hydrolyze for 1~2 h; cooling to 40~65° C., adjusting to pH 3.0~5.5, and adding glucoamylase to hydrolyze for 10~20 h.

Step 3: performing solid-liquid separation to the liquid material, concentrating the liquid to obtain the product of liquid sugar, the ingredient of which is basically glucose.

As a preference, the pulverizing in step 1 is performed at a screen aperture of 830 μm~150 μm.

As a preference, the formulating of slurry is to mix at a material-to-liquid mass ratio of 1:4~6.

As a preference, in step 1, 70~200 U cellulase is added for each gram of material.

As a preference, in step 1, 4.5~13.5 U β-glucanase is added for each gram of material.

As a preference, in step 2, 14.5~29 U xylanase is added for each gram of material, and 9~30 U pectinase is added for each gram of material.

As a preference, in step 2, 10~15 U acid protease is added for each gram of material.

As a preference, in step 2, 12~20 U thermostable α-amylase is added for each gram of material.

As a preference, in step 2, 100~300 U glucoamylase is added for each gram of material.

As a preference, an additional step is comprised after step 2 and before step 3: adjusting to pH 5.5~8.0, adding thermostable α-amylase for the second liquidification for 45 min; cooling to 40~65° C., adjusting to pH 3.0~5.5, adding glucoamylase and cellulase to perform saccharification. As a preference, 100 U glucoamylase is added for each gram of material, and 70 U cellulase is added for each gram of material.

Preparing sugar from sweet potato residue by enzymatic method according to the present method, using commercially available domestic cellulase, β-glucanase, xylanase and pectinase, acid protease, thermostable α-amylase, glucoamylase, and comparing different liquid materials. The conversion rate of dry matter in sweet potato residue to glucose is above 65%, and the conversion rate of starch in sweet potato residue to the reducing sugar can reach 110%. The conversion rate is greatly increased as compared to the traditional double-enzyme method. The conversion rate of enzymatic hydrolysis refers to the mass fraction of total amount (calculated by glucose) of reducing sugars released by enzymatic hydrolysis of sweet potato residue to the mass of dry matter in the test sweet potato residue, which indicates the hydrolysis degrees of various polysaccharides (starch and pectin, hemicellulose and cellulose, etc.) in the sweet potato residue.

Experiments indicate that it is technically difficult to hydrolyze various polysaccharide components in sweet potato residue by using domestic enzyme preparations, particularly the conversion rate for preparing sugar by degrading cellulose and lignin is low. The mechanism for the combined enzymolysis according to the present invention is that cellulase, β-glucanase, pectinase and xylanase synergistically act to destroy the cell wall, disconnect the linked lignin and pectin (the matrix that protects cellulose) and glycoprotein in binding state. The biochemical reactions of degrading various components of polysaccharide macromolecules in the sweet potato residue into monosaccharide are enzymatically promoted, to increase the conversion rate.

The sweet potato residue contains 50% or more starch (based on dry matter), and the polysaccharides of hemicellulose and pectin in loose structure can be transformed into sugar completely or partially by hydrolytic enzymes. The samples prepared by the method according to the present invention are analyzed by HPAEC (Dionex Corporation): selecting PA10 analytical column and using 18 mM NaOH as buffer, flow rate: 1 ml/min, collecting for 40 min for each sample. The samples are identified to be basically glucose, which are high-quality sugar materials for microbial fermentation, and can be used in industrial fermentation.

The liquid sugar components prepared using the present process are identified by Chinese Academy of Sciences (CAS) to be basically glucose, rather than other reducing monosacchrides, indicating that the preparation process can basically reach a complete enzymolysis.

The method according to the present invention is mild in processing conditions, simple in processing and equipment, strong in specificity, and improves the conversion rate of total reducing sugar, and the products are pure in quality. Such method can solve the problem of severe environmental pollution, and has good prospects for industrial applications.

DETAILED EMBODIMENTS

The present invention discloses a method for preparing sugar from sweet potato residue. Those skilled in the art can use the contents herein for reference, and appropriately improve the processing parameters to achieve. It needs to be particularly noted that all the similar substitutions and alterations are obvious to those skilled in the art, and they are all deemed to be included in the present invention. The methods and applications of the present invention have been described by preferred examples. Related skilled personnel can modify or appropriately change and combine the methods and applications described herein to achieve and apply the techniques of the present invention, without departing from the contents, spirit, and scope of the present invention.

In order to further understand the technical solution of the present invention, the present invention is further illustrated below in details, in conjunction with specific examples.

EXAMPLE 1

Sweet potato residue (moisture 12.7%, starch 56.19%, crude protein 3.69%) were obtained from certain place in Shandong Province, pulverized into 250 µm screen aperture, prepared into a slurry according to a material-liquid ratio of 1:5 in a 30 L pot by adding waste water of sweet potato starch. The slurry was adjusted to pH 5.5, warmed to 55° C., and hydrolyzed for 4 h after adding cellulase (100 U enzyme was added for each gram of material) and adding β-glucanase (10 U enzyme was added for each gram of material). Then, the slurry was cooled to 45° C., adjusted to pH 4.5, and hydrolyzed for 4 h after adding xylanase and pectinase (29 U xylanase and 20 U pectinase were added for each gram of material).

Acid protease (10 U enzyme was added for each gram of material) was added and hydrolyzed for 2 h at a temperature of 50° C. and pH 4.0. The temperature was raised to 110° C. to inactivate the enzyme. The pH was adjusted to 6.5, and thermostable α-amylase was added (12 U enzyme was added for each gram of material) to liquify for 45 min. The temperature was cooled to 60° C., the pH was adjusted to 4.5, and glucoamylase (200 U enzyme was added for each gram of material) was hydrolyzed for 10 h. The batch of pots for enzymolysis was directly adjusted to pH 6.5, and thermostable α-amylase (12 U enzyme was added for each gram of material) was added, and liquification was performed for the second time for 60 min. The temperature was cooled to 60° C., the pH was adjusted to 4.5, glucoamylase (100 U enzyme was added for each gram of material) and cellulase (100 U enzyme was added for each gram of material) were added to perform saccharification.

After completing the saccharification, the liquid material was subjected to solid-liquid separation, and the liquid was concentrated to obtain the product of liquid sugar. The conversion rate of the dry matter of sweet potato residue to glucose was 65.6%. The conversion rate of "starch" in the sweet potato residue to monosaccharide was 108%.

The content of starch in the sweet potato residue was calculated according to the content determination of starch in food and oil of "National Standards GB/T 5514-2008". The method is as follows: quantitatively weighing sweet potato residue which have been determined for the "starch" content, centrifuging the saccharized mash after hydrolyzing, washing and centrifuging, measuring and recording the total amount of reducing sugars in the supernatant, and calculating the conversion rate according to the following equation:

Conversion rate of mass of the sweet potato residue (by dry weight) to sugar (%)=[total amount of reducing sugar in supernatant (by dry weight) ÷mass of sweet potato residue (by dry weight)]×100

EXAMPLE 2

Sweet potato residue (moisture 12.7%, starch 56.19%, crude protein 3.69%) were obtained from certain place in Shandong Province, pulverized into 380 µm screen aperture, prepared into a slurry according to a material-liquid ratio of 1:4.5 in a 30 L pot by adding waste water of sweet potato starch. The slurry was adjusted to pH 5.0, warmed to 50° C., and hydrolyzed for 4 h after adding cellulase (70 U enzyme was added for each gram of material) and adding β-glucanase (10 U enzyme was added for each gram of material). Then, the slurry was cooled to 42° C., adjusted to pH 4.0, and hydrolyzed for 4 h after adding xylanase and pectinase (14.5 U xylanase and 9 U pectinase were added for each gram of material).

Acid protease (12 U enzyme was added for each gram of material) was added and hydrolyzed for 2 h at a temperature of 50° C. and pH 4.0. The temperature was raised to 115° C. to inactivate the enzyme. The pH was adjusted to 6.5, and thermostable α-amylase was added (15 U enzyme was added for each gram of material) to liquify for 45 min. The temperature was cooled to 60° C., the pH was adjusted to 4.5, and glucoamylase (100 U enzyme was added for each gram of material) was hydrolyzed for 15 h. The batch of pots for enzymolysis were directly adjusted to pH 6.5, and thermostable α-amylase (12 U enzyme was added for each gram of material) was added, and liquification was performed for the second time for 45 min. The temperature was cooled to 60° C., the pH was adjusted to 4.5, glucoamylase (100 U enzyme was added for each gram of material) and cellulase (100 U enzyme was added for each gram of material) were added to perform saccharification.

After completing the saccharification, the liquid material was subjected to solid-liquid separation, and the liquid was concentrated to obtain the product of liquid sugar. The conversion rate of the dry matter of sweet potato residue to glucose was 65.2%. The conversion rate of "starch" in the sweet potato residue to monosaccharide was 106%.

EXAMPLE 3

Sweet potato residue (moisture 12.7%, starch content >62%, crude protein 3.69%) were obtained from certain place in Shandong Province, pulverized into 230 um screen aperture, prepared into a slurry according to a material-liquid ratio of 1:4 in a 30 L pot by adding waste water of sweet potato starch. The slurry was adjusted to pH 6.0, warmed to 60° C., and hydrolyzed for 4 h after adding cellulase (200 U enzyme was added for each gram of material) and adding β-glucanase (13.5 U enzyme was added for each gram of material). Then, the slurry was cooled to 50° C., adjusted to pH 4.6, and hydrolyzed for 4 h after adding xylanase and pectinase (20 U xylanase and 30 U pectinase were added for each gram of material).

Acid protease (15 U enzyme was added for each gram of material) was added and hydrolyzed for 2 h at a temperature of 50° C. and pH 4.0. The temperature was raised to 120° C. to inactivate the enzyme. The pH was adjusted to 6.5, and thermostable α-amylase was added (20 U enzyme was added for each gram of material) to liquify for 50 min. The temperature was cooled to 60° C., the pH was adjusted to 4.5, and glucoamylase (300 U enzyme was added for each gram of material) was hydrolyzed for 20 h. The batch of pots for enzymolysis were directly adjusted to pH 6.5, and thermostable α-amylase (12 U enzyme was added for each gram of material) was added, and liquification was performed for the second time for 45 min. The temperature was cooled to 60° C., the pH was adjusted to 4.5, glucoamylase (100 U enzyme was added for each gram of material) and cellulase (100 U enzyme was added for each gram of material) were added to perform saccharification.

After completing the saccharification, the liquid material was subjected to solid-liquid separation, and the liquid was concentrated to obtain the product of liquid sugar. The conversion rate of the dry matter of sweet potato residue to glucose was 68.4%. The conversion rate of "starch" in the sweet potato residue to monosaccharide was 110%.

EXAMPLE 4

The liquid sugar product of any of Example 1-3 was taken for analysis

Sample Treatment:

12000 rpm, 10 min. Supernatant was taken, and filtered through 0.45 μm Pal membrane.

Sample analysis: HPAEC analysis from Dionex Corporation, PA10 analytical column was selected.

Buffer: 18 mM NaOH

Flow rate: 1 ml/min

The collecting time for each sample is 40 min.

Experimental Results:

Monosacchrides which might be contained in the selected samples were used as standards, and analyzed in PA10. The retention times for monosacchrides are shown in Table 1.

TABLE 1

| Retention time for monosacchrides | | | | | | |
|---|---|---|---|---|---|---|
| | Rhamnose | Arabinose | Galactose | Glucose | Xylose | Mannose |
| Retention time | 8.417 | 9.417 | 11.25 | 13 | 13.583 | 14.083 |

It was verified that xylose and mannose cannot be separated under this condition, so that the retention time of 13.5 min is for the mixture of xylose and mannose.

Analysis of Liquid Sugar Components

Sampling: samples were taken from the same batch of pots after hydrolyis by adding different enzymes in chronological order.

Code 1#: 0~10 h, cellulase and β-glucanase were added (4 h); then xylanase and pectinase were added (4 h); acid protease was further added (2 h), and then sampled and centrifuged to obtain the centrifuged supernatant.

Code 2#: 10 h~11 h (to follow 1# process) and then the centrifuged supernatant hydrolyzed by α-amylase was added.

Code 3#: the concentrate of the centrifuged supernatant of 2# liquified liquid material.

Code 4#: 11 h~26 h (to follow 2# process) and then the centrifuged supernatant of the saccharized liquid material hydrolyzed by glucoamylase (i.e., the liquid sugar product obtained by any of Examples 1-3)

Code 5#: the concentrate of the 4# centrifuged supernatant of saccharized liquid 1, 2, 3, 4# samples were all diluted for 100 times and the 5# sample was diluted for 200 times, and they were tested by Bioengineering Center for Sugar, Institute of Microbiology, CAS: analyzed by HPAEC of Dionex Corporation, and PA10 analytical column was selected. Standards for rhamnose, arabinose, galactose, glucose, xylose and mannose were used for the test.

There were two peaks for 1# sample: 8.667 and 11.917, and the content of glucose was 10.5 mg/ml. The content of arabinose very little.

The major peak time for 2# was 11.750, and the content was 172 mg/ml.

3# sample: 11.417, and the content of sugar was 548 mg/ml.

4# sample: 11.583. The content of sugar was 184 mg/ml, and no disaccharide and polysaccharide was detected.

5# sample: 11.5. The content of sugar was 511 mg/ml, and no disaccharide and polysaccharide was detected.

Preliminary analysis of the results: the majority of component in the samples was glucose, i.e., except for the 1# sample before the "liquified process" which contains trace amount of rhamnose and glucose, the components of the four samples in the other processes were all glucose, that is the components of centrifuged supernatant of the saccharized liquid material were all glucose. In summary, all the components of the samples of liquid sugar product obtained according to any of Examples 1-3 were basically all glucose.

The process for preparing sugar by enzymatically hydrolyzing sweet potato residue provided by the present invention are described above in details. The principles and embodiments of the present invention were illustrated herein by using specific examples, and the illustrations to the above examples are used for facilitating the understanding of the methods and the core idea of the present invention. It should be noted that, the present invention can be improved and modified by those skilled in the art, without departing from the principle of the present invention. These improvements and modifications also fall within the protection scope of the claims of the present invention.

The invention claimed is:

1. A method for preparing sugar by using sweet potato residue, characterized in that the method comprises the following steps:
   (a) taking sweet potato residue, pulverizing or grinding the wet residue, adding the waste water of sweet potato starch to formulate a slurry; adjusting the slurry to pH 4.0~6.0, adding cellulase and adding β-glucanase to hydrolyze for 2~10 h at 20~70° C.; then
   (b) adding xylanase and pectinase to hydrolyze for 2~10 h at 25~60° C. and pH 3.5~6.0; adding acid protease to hydrolyze for 1~8 h at a temperature of 30~50° C. and pH 2.5~6.0; heating at 110~120° C. for 30 min to inactivate the enzymes; adjusting to pH 5.5~8.0, adding thermostable α-amylase or mesophilic α-amylase to hydrolyze for 1~2 h; cooling to 40~65° C., adjusting to pH 3.0~5.5, and adding glucoamylase to hydrolyze for 10~20 h; and then
   (c) performing solid-liquid separation on the slurry material and concentrating the liquid to obtain glucose.

2. The method according to claim 1, characterized in that the pulverizing in step (a) is performed at a screen aperture of 150 μm ~830 μm.

3. The method according to claim 1, characterized in that the formulating of slurry in step (a) is performed by mixing at a material-to-liquid mass ratio of 1:4~6.

4. The method according to claim 1, characterized in that, in step (a), 70~200 U cellulose is added for each gram of material.

5. The method according to claim 1, characterized in that, in step (a), 4.5~13.5 U β-glucanase is added for each gram of material.

6. The method according to claim 1, characterized in that, in step (b), 14.5~29 U xylanase is added for each gram of material, and 9~30 U pectinase is added for each gram of material.

7. The method according to claim 1, characterized in that, in step (b), 10~15 U acid protease is added for each gram of material.

8. The method according to claim 1, characterized in that, in step (b), 12~20 U thermostable α-amylase is added for each gram of material.

9. The method according to claim 1, characterized in that, in step (b), 100~300 U glucoamylase is added for each gram of material.

10. The method according to claim 1, further comprising an additional step after step (b) adjusting to pH 5.5~8.0, adding thermostable α-amylase for the second liquidification for 45 min; cooling to 40~65° C., adjusting to pH 3.0~5.5, and adding glucoamylase and cellulase to perform saccharification.

11. The method according to claim 10, characterized in that, 100~300 U glucoamylase is added for each gram of material, and 70~200 U cellulose is added for each gram of material.

* * * * *

UNITED STATES PATENT AND TRADEMARK OFFICE
CERTIFICATE OF CORRECTION

PATENT NO. : 9,506,096 B2
APPLICATION NO. : 14/385817
DATED : November 29, 2016
INVENTOR(S) : Yunshan Wu et al.

It is certified that error appears in the above-identified patent and that said Letters Patent is hereby corrected as shown below:

In the Claims

In Claim 2, Column 8, Line 7, delete "step (a)is" and replace with --step (a) is-- therefor.

In Claim 3, Column 8, Line 10, delete "step (a)is" and replace with --step (a) is-- therefor.

In Claim 10, Column 8, Line 32, delete "step (b)adjusting" and replace with --step (b) of adjusting-- therefor.

Signed and Sealed this
Twenty-eighth Day of February, 2017

Michelle K. Lee
*Director of the United States Patent and Trademark Office*